(12) United States Patent
Kelemen et al.

(10) Patent No.: US 12,105,083 B2
(45) Date of Patent: Oct. 1, 2024

(54) METHODS FOR DETECTING ANTIBODIES BY SURFACE PLASMON RESONANCE

(71) Applicant: Laboratory Corporation of America Holdings, Burlington, NC (US)

(72) Inventors: Mary Katherine Morr Kelemen, Thousand Oaks, CA (US); Brett Holmquist, Thousand Oaks, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 911 days.

(21) Appl. No.: 16/850,541

(22) Filed: Apr. 16, 2020

(65) Prior Publication Data
US 2020/0333331 A1 Oct. 22, 2020

Related U.S. Application Data

(60) Provisional application No. 62/834,649, filed on Apr. 16, 2019.

(51) Int. Cl.
*G01N 33/543* (2006.01)
*G01N 21/552* (2014.01)
(Continued)

(52) U.S. Cl.
CPC ......... *G01N 33/543* (2013.01); *G01N 21/553* (2013.01); *G01N 33/54353* (2013.01);
(Continued)

(58) Field of Classification Search
CPC .............. G01N 33/543; G01N 21/553; G01N 33/54353; G01N 33/548; G01N 33/553;
(Continued)

(56) References Cited

U.S. PATENT DOCUMENTS

| 5,242,828 A * | 9/1993 | Bergstrom ....... G01N 33/54353 435/287.7 |
| 9,759,732 B2 * | 9/2017 | Grabert ............. G01N 33/6854 |
| 2016/0097777 A1 * | 4/2016 | Bill ........................ G01N 33/94 435/7.92 |

FOREIGN PATENT DOCUMENTS

| CA | 3015711 A1 | 10/2017 |
| EP | 1 347 300 A1 | 9/2003 |

(Continued)

OTHER PUBLICATIONS

Beeg et al, "A Surface Plasmon Resonance-based assay to measure serum concentrations of therapeutic antibodies and anti-drug antibodies", Scientific Reports, Published online Feb. 14, 2019, pp. 1-9 (Year: 2019).*

(Continued)

*Primary Examiner* — Christopher L Chin
(74) *Attorney, Agent, or Firm* — Kilpatrick Townsend & Stockton LLP (57) ABSTRACT

The present disclosure relates to a method for detection of an antibody or antibody fragment in a biological sample from a subject. In some embodiments, the methods comprise immobilizing a first binding agent on a surface plasmon resonance (SPR) biosensor; adding a ligand that binds to the first binding agent under conditions such that a complex of the ligand and the first binding agent is formed; adding an aliquot of the biological sample under conditions such that the antibody and/or antibody fragment binds to the ligand that is complexed to the first binding agent; and detecting the presence of the antibody and/or antibody fragment as a change in signal obtained from SPR. In some embodiments, the antibody is an antibody therapeutic such as certolizumab pegol. Also disclosed are systems and kits for detecting an antibody in a biological sample from a subject using SPR.

15 Claims, 2 Drawing Sheets

(51) Int. Cl.
  *G01N 33/548* (2006.01)
  *G01N 33/553* (2006.01)
  *G01N 33/68* (2006.01)
(52) U.S. Cl.
  CPC ......... *G01N 33/548* (2013.01); *G01N 33/553* (2013.01); *G01N 33/6854* (2013.01)
(58) Field of Classification Search
  CPC ......... G01N 33/6854; G01N 33/54373; G01N 33/54306; G01N 2021/5903; G01N 2333/525
  USPC ............ 356/317, 318; 422/82.11; 435/288.7; 436/164, 525, 805
  See application file for complete search history.

(56) References Cited

FOREIGN PATENT DOCUMENTS

| EP | 2378289 A1 | 10/2011 |
|---|---|---|
| WO | 2013/066986 A1 | 5/2013 |

OTHER PUBLICATIONS

Goel et al, "Certolizumab pegol", mAbs, 2:2, 137-147; Mar./Apr. 2010, 137-147 (Year: 2010).*

Davidoff et al, "Surface Plasmon Resonance for Therapeutic Antibody Characterization", Methods in Pharmacology and Toxicology, Springer Protocols: Label-Free Biosensor Methods in Drug Discovery, 2015, pp. 35-76 (Year: 2015).*

PCT/US2020/028485, International Preliminary Report on Patentability, Oct. 28, 2021, 8 pages.

Canoa, P. et al., "Use of Surface Plasmon Resonance in the Binding Study of Vitamin D, Metabolites and Analogues with Vitamin D Binding Protein", Anal. Bioanal. Chem., 409(10):2547-2558 (2017).

Hendriks, J. et al., "Nanoparticle Enhancement Cascade for Sensitive Multiplex Measurements of Biomarkers in Complex Fluids with Surface Plasmon Resonance Imaging", Anal. Chem., 90(11):6563-6571 (2018).

Ogura, T. et al., "Whole Cell-Based Surface Plasmon Resonance Measurement to Assess Binding of Anti-TNF Agents to Transmembrane Target", Analytical Biochemistry, 508:73-77 (2016).

International Patent Application No. PCT/US2020/028485, International Search Report and Written Opinion, Jul. 17, 2020, 12 pages.

Antibodies: A Laboratory Manual, Cold Spring Harbor Laboratory, Harlow, E. and Lane, D. eds., Cold Spring Harbor Press, Cold Spring Harbor, NY, 1988.

Basic Methods in Antibody Production and Characterization, 2001 (Howard and Bethell eds.), CRC Press.

The Immunoassay Handbook, 1994 (Wild ed.), Stockton Press, New York, NY.

CA3,136,161 , "Office Action", Jan. 3, 2023, 9 pages.
CA3,136,161 , "Office Action", Sep. 27, 2023, 3 pages.
EP20729864.7 , "Office Action", Jan. 20, 2023, 4 pages.
EP20729864.7 , "Office Action", Sep. 25, 2023, 6 pages.

Lu , et al., "Fiber Optic-spr Platform for Fast and Sensitive Infliximab Detection in Serum of Inflammatory Bowel Disease Patients", Biosensors and Bioelectronics, vol. 79, May 1, 2016, pp. 173-179.

EP20729864.7, "Office Action", dated May 22, 2024, 4 pages.
CN202080036646.9, "Office Action", dated Jul. 15, 2024, 15 pages.

* cited by examiner

METHODS FOR DETECTING ANTIBODIES BY SURFACE PLASMON RESONANCE

PRIOR RELATED APPLICATIONS

The present application claims priority to U.S. provisional patent application No. 62/834,649, filed Apr. 16, 2019, the contents of which is incorporated by reference herein in its entirety.

BACKGROUND

Therapeutic antibodies are becoming a more common method of treatment in conditions such as cancer and autoimmune diseases. However, while one patient may benefit from treatment with a therapeutic antibody, another may have no response to treatment or find that the treatment becomes less efficacious over time. This can be caused by both sub-optimal dosing and/or premature clearance of the therapeutic antibodies by anti-drug antibodies. Optimizing a patient's dosage requires measuring the therapeutic antibody's concentration in the patient's blood. However, current testing methods are expensive, time consuming, and of questionable accuracy.

SUMMARY

The present disclosure relates to a method for detection of an antibody and/or a fragment of an antibody in a biological sample from a subject. In some embodiments, disclosed are methods for detection of an antibody and/or antibody fragment in a biological sample from a subject comprising immobilizing a first binding agent on a surface plasmon resonance (SPR) biosensor; adding a ligand that binds to the first binding agent under conditions such that a complex of the ligand and the first binding agent is formed; adding an aliquot of the biological sample under conditions such that the antibody and/or antibody fragment binds to the ligand that is complexed to the first binding agent; and detecting the presence of the antibody and/or antibody fragment as a change in signal obtained from SPR.

In some embodiments, the antibody is an antibody therapeutic. In some embodiments, the antibody is certolizumab pegol.

In some embodiments, the method further comprises adding a secondary antibody or a second binding agent that recognizes a moiety of the antibody and/or antibody fragment prior to detecting the final signal obtained from SPR.

In some embodiments, the method further comprises adjusting the amount of the antibody in the subject based on the amount detected in the biological sample.

Also disclosed are systems and kits for detecting an antibody or a fragment thereof in a biological sample from a subject using SPR.

DETAILED DESCRIPTION

The following description recites various aspects and embodiments of the disclosed methods, systems, and kits. No particular embodiment is intended to define the scope of the methods, systems, or kits. Rather, the embodiments merely provide non-limiting examples that are at least included within the scope of the disclosed methods, systems, and kits. The description is to be read from the perspective of one of ordinary skill in the art; therefore, information well known to the skilled artisan is not necessarily included.

Definitions

The present disclosure now will be described more fully hereinafter. The disclosure may be embodied in many different forms and should not be construed as limited to the aspects set forth herein; rather, these aspects are provided so that this disclosure will satisfy applicable legal requirements. Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

When introducing elements of the present disclosure or the embodiment(s) thereof, the articles "a", "an", "the" and "said" are intended to mean that there are one or more of the elements. The terms "comprising", "including" and "having" are intended to be inclusive and mean that there may be additional elements other than the listed elements. It is understood that aspects and embodiments of the disclosure described herein include "consisting" and/or "consisting essentially of" aspects and embodiments.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The term "antibody" means an immunoglobulin that binds to, and is thereby defined as complementary with, a particular spatial and polar organization of another molecule. The antibody can be monoclonal, polyclonal, or recombinant and can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for binding. Antibodies may include a complete immunoglobulin or fragment thereof, which immunoglobulins include the various classes and isotypes, such as IgA, IgD, IgE, IgG1, IgG2a, IgG2b and IgG3, IgM, etc. The term "antibody fragment" refers to antigen-binding fragments of antibodies. These fragments may include Fab, Fv and F(ab')2, Fab' and the like. Antibodies (and fragments derived therefrom) may also be single-chain antibodies, chimeric antibodies, humanized antibodies or any other antibody derivative known to one of skill in the art that retains binding activity that is specific for a particular binding site. In addition, aggregates, polymers and conjugates of immunoglobulins or their fragments can be used where appropriate so long as binding affinity for a particular binding site is maintained. Guidance in the production and selection of antibodies and antibody derivatives for use in immunoassays, including such assays employing releasable molecular tags (as described below) can be found in readily available texts and manuals, e.g., Harlow and Lane, 1988, Antibodies: A Laboratory Manual, Cold Spring Harbor Laboratory Press, New York; Howard and Bethell, 2001, Basic Methods in Antibody Production and Characterization, CRC Press; Wild, ed., 1994, The Immunoassay Handbook, Stockton Press, New York.

The term "Antibody therapeutics" or "therapeutic antibodies" refers to antibodies that can activate, repress, or alter endogenous immune responses to specific cells or molecules. In some embodiments, therapeutic antibodies are monoclonal antibodies. These antibody-based drugs can be used to treat cancer, inflammatory and autoimmune diseases, as well as other types of diseases.

The term "binding compound" refers to a molecule capable of binding to another molecule. A binding compound may be an antibody, a peptide, a peptide or non-peptide ligand for a cell surface receptor, a protein, an oligonucleotide, an oligonucleotide analog, such as a peptide nucleic acid, a lectin or any other molecular entity that is capable of specifically binding to a target molecule or complex.

The term "binding moiety" refers to any molecule that is capable of binding to an analyte. Binding moieties include, but are not limited to, antibodies, peptides, proteins, nucleic acids and organic molecules.

The term "epitope" refers to a site on the surface of a molecule, usually a protein, to which an antibody molecule or other binding compound binds. Generally, a protein has several or many different epitopes, also called antigenic determinants, and reacts with antibodies of different specificities.

The term "sample" includes "biological sample." The term "biological sample" refers to a sample obtained from a biological source, including, but not limited to, an animal, a cell culture, an organ culture, and the like. Suitable samples include blood, plasma, serum, urine, saliva, tear, cerebrospinal fluid, organ, hair, muscle, or other tissue sample. Or, a sample may not be a biological sample but may be a synthetic (i.e., in vitro) sample, as for example for the analysis of a synthesis product or enzymatic reaction. In other embodiments, the terms "sample" or "biological sample" or "tissue sample" or "patient sample" or "patient cell or tissue sample" or "specimen" may each refer to a collection of similar cells obtained from a tissue of a subject or patient. The source of the tissue sample may be solid tissue as from a fresh tissue, frozen and/or preserved organ or tissue or biopsy or aspirate; blood or any blood constituents, bodily fluids such as cerebral spinal fluid, amniotic fluid, peritoneal fluid or interstitial fluid or cells from any time in gestation or development of the subject. The tissue sample may contain compounds that are not naturally intermixed with the tissue in nature such as preservatives, anticoagulants, buffers, fixatives, nutrients, antibiotics or the like. Cells may be fixed in a conventional manner, such as in an FFPE manner.

The terms "subject" and "patient" are used interchangeably herein. The terms "subject" and "subjects" refer to an animal, preferably a mammal including a non-primate (e.g., a cow, pig, horse, donkey, goat, camel, cat, dog, guinea pig, rat, mouse or sheep) and a primate (e.g., a monkey, such as a cynomolgus monkey, gorilla, chimpanzee or a human).

The term "treatment," and other forms of this word refer to the administration of an agent to impede a disease. Treatment may also refer to any course which one skilled, for example, a treating physician, deems expedient.

The term "specificity" refers to the ability of the measurement procedure to discriminate the analyte when presented with substances potentially found within a sample. In an embodiment, it is expressed as a percent (%) cross-reactivity and/or response to substances other than analyte in the absence of the analyte.

The term "selectivity" refers to the ability of the measurement procedure to accurately measure the analyte without contribution of the substances potentially found within a sample. In an embodiment, it is expressed as a % cross-reactivity and/or response to substances other than analyte in the presence of the analyte.

The term "surface plasmon resonance" refers to the physical process that can occur when plane-polarized light hits a thin metal film under total internal reflection conditions. Resonant oscillation of conduction electrons—plasmons—in the thin metal film is caused by this incident light stimulation.

The term "Limit of Blank" (LOB) refers to the highest measurement result that is likely to be observed for a blank samples (with a stated probability). LOB is typically expressed as mean plus 1.645×Standard Deviation (SD) (or 2×SD) of blank measurements.

The term "Limit of Detection" (LOD) refers to the lowest amount of analyte in a sample that can be detected (with stated probability). LOD is typically expressed as LOB plus 1.645×SD (or 2×SD) of low sample measurements.

The term "Lower Limit of Quantitation" (LLOQ) refers to the lowest amount of analyte in a sample that can be quantitatively determined with stated acceptable precision and accuracy.

The term "Upper Limit of Quantitation" (ULOQ) refers to the highest amount of analyte in a sample that can be quantitatively determined without dilution.

The term "intra-run imprecision" refers to the closeness of the agreement between the results of successive measurements carried out under the same conditions of measurements (i.e., during the same analytical run).

The term "inter-run imprecision" refers to the closeness of the agreement between independent test results obtained under stipulated conditions (different analytical runs and/or operators, laboratories, instruments, reagent lots, calibrators, etc.).

Methods of Detecting

The present disclosure relates to methods for detecting antibodies or antibody fragments in a biological sample. The methods may be embodied in a variety of ways.

In some embodiments, the method for detection of an antibody and/or antibody fragment in a biological sample from a subject may comprise immobilizing a first binding agent on a surface plasmon resonance (SPR) biosensor; adding a ligand that binds to the first binding agent under conditions such that a complex of the ligand and the first binding agent is formed; adding an aliquot of the biological sample under conditions such that the antibody and/or antibody fragment binds to the ligand that is complexed to the first binding agent; and detecting the presence of the antibody and/or antibody fragment as a change in signal obtained from SPR.

In some embodiments, the first binding agent is an antibody. In some embodiments, the first binding agent is an anti-TNFα antibody and the ligand is TNFα. In some embodiments, the method comprises not using a first binding agent and immobilizing the ligand on the SPR biosensor. In some embodiments, the ligand immobilized to the SPR biosensor is TNFα.

Figure 1:
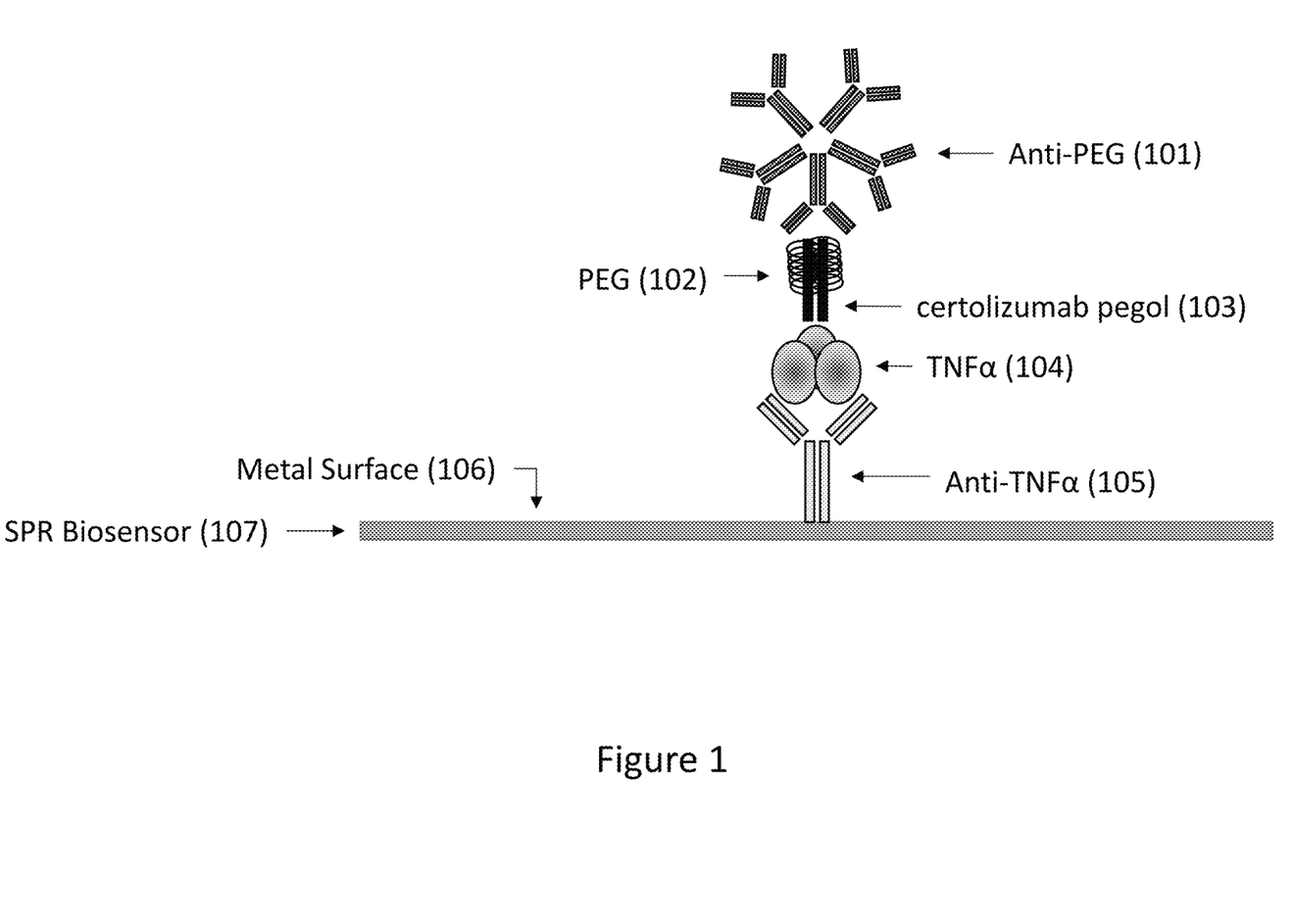
FIG. 1 illustrates a first binding agent (105), a ligand (104), an antibody (103), and a second binding agent (101) complexed on the metal surface (106) of an SPR biosensor (107) in accordance with an embodiment of the disclosure.

Alternatively, in some embodiments, the method further comprises adding a secondary antibody or a second binding agent that recognizes a moiety on the antibody and/or antibody fragment present in the sample prior to detecting the final signal obtained from SPR. The secondary binding agent or antibody may be used in the embodiment where a first binding agent is used or in the embodiment where the first binding agent is not used (i.e., where the ligand is immobilized directly to the SPR biosensor). For example, FIG. 1 depicts an embodiment of the disclosure wherein a first binding agent (105), a ligand (104), an antibody (103), and a secondary antibody (101) are complexed on the surface (106) of an SPR biosensor (107). In some embodiments of the present disclosure, the moiety on the antibody (103) is polyethylene glycol (PEG) (102).

In some embodiments, the antibody or antibody fragment being detected is an antibody therapeutic. In some embodiments, the antibody therapeutic is certolizumab pegol. In some embodiments, the moiety on the antibody is polyethylene glycol (PEG). In some embodiments, the ligand is TNFα. In some embodiments, the first binding agent is an antibody.

In some embodiments, the method further comprises adjusting the amount of the antibody or fragment thereof in the subject (i.e. the therapeutic dose) based on the amount detected in the biological sample.

In some embodiments, the surface plasmon resonance (SPR) provides for real-time detection of the antibody. In some embodiments, the SPR biosensor comprises a sensor chip. In some embodiments, the SPR biosensor comprises a metal surface. In some embodiments, the SPR biosensor comprises a thin alginate layer for amine coupling of ligands. In some embodiments, the sensor chip has a surface coating that can be activated to react specifically with free surface amines of proteins. Or, as detailed herein, other types of couplings may be used. In some embodiments, activation refers to the priming of the sensor chip so it can form a covalent bond with another molecule. In some embodiments, the ligand is immobilized at a density of at least 1,000 Response Units (RU).

In some embodiments, the biological sample is serum or plasma. In some embodiments, the biological sample is from a human. In some embodiments, the biological sample is diluted prior to being added to the SPR biosensor. In some embodiments the biological sample is diluted 2-fold. In some embodiments, the biological sample is diluted up to 10-fold. In some embodiments, the sample is diluted up to 20-fold. In some embodiments, the sample is diluted up to 100-fold.

In some embodiments, the subject is being treated with an antibody therapeutic. In some embodiments, the method further comprises adjusting the amount of the antibody or fragment thereof in the subject based on the amount detected in the biological sample.

In some embodiments, the intra-assay inaccuracy is less than 20%. In some embodiments, the acceptable detected concentration of an antibody is 80-120% of its actual concentration. In some embodiments, the sensitivity for measurement of an antibody or antibody fragment is affected less than 5% by the presence of an interferent. In some embodiments, the LLOQ and ULOQ for certolizumab are 1.0 μg/mL and 90 μg/mL, respectively.

In some embodiments, the method further comprises use of a computer or computer-program product to implement any of the steps of the method.

Systems and Kits

In another embodiment, the disclosure comprises a system for detecting an antibody or antibody fragment in a biological sample from a subject. In some embodiments the system for detection of an antibody or antibody fragment in a biological sample from a subject may comprise a biosensor for surface plasmon resonance (SPR) having a first binding agent immobilized on one surface; a ligand for the first binding agent, wherein the ligand also binds to the antibody or antibody fragment; and a component for measuring a signal from the biosensor for surface plasmon resonance. In some embodiment, the system may also comprise a second antibody or a second binding agent that recognizes a moiety on the antibody. In some embodiments, the system may also comprise reagents for washing the biosensor to remove biomolecules that do not specifically bind to the first binding agent, the ligand, or the antibody. In some embodiments, the ligand is immobilized directly on the biosensor surface, without the use of a first binding agent. The secondary binding agent or antibody may be used in the embodiment where a first binding agent is used or in the embodiment where the first binding agent is not used (i.e., where the ligand is immobilized directly to the SPR biosensor).

Figure 2:
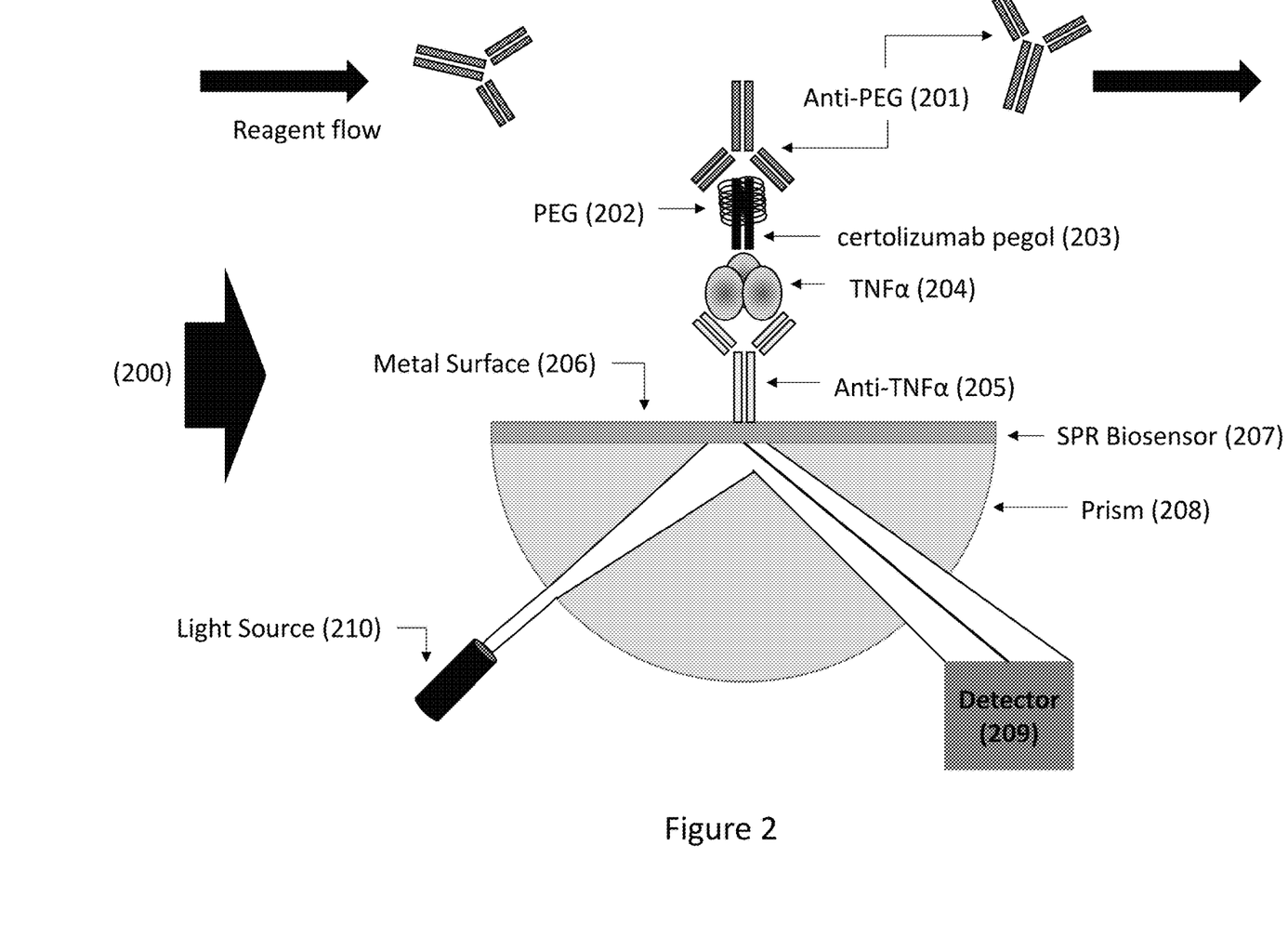
FIG. 2 illustrates a system (200) for detecting an antibody (203) in a biological sample from a subject using SPR in accordance with an embodiment of the disclosure.

As is depicted in FIG. 2, in some embodiments, the system (200) for detecting an antibody or antibody fragment may comprise a biosensor for SPR (207) having a first binding agent (205) immobilized on one surface; a ligand (204) for the first binding agent (205), wherein the ligand (204) also binds to the antibody (203); optionally, a second antibody (201) or a second binding agent that recognizes a moiety (202) on the antibody (203); and optionally, reagents for washing the biosensor to remove biomolecules that do not specifically bind to the first binding agent (205), the ligand (204), or the antibody (203). FIG. 2 depicts the addition of a second antibody (201) to an embodiment of the system.

In some embodiments, the antibody or antibody fragment is an antibody therapeutic. In some embodiments of the system, the antibody therapeutic is certolizumab. In some embodiments of the system, the moiety on the antibody is polyethylene glycol (PEG). In some embodiments of the system, the ligand is TNFα. In some embodiments of the system, the first binding agent is an antibody to TNFα and/or the second antibody is an antibody to PEG.

In some embodiments of the system, surface plasmon resonance (SPR) provides for real-time detection of the antibody. In some embodiments of the system, the SPR biosensor comprises metal surface. In some embodiments of the system, the SPR biosensor comprises a sensor chip. In some embodiments of the system, the SPR biosensor comprises a thin alginate layer for amine coupling of ligands. In some embodiments of the system, the sensor chip has a surface coating that can be activated to react specifically with free surface amines of proteins. Or, other types of couplings may be used. In some embodiments of the system, the ligand is immobilized at a density of at least 1,000 Response Units (RU). In some embodiments, the ligand is immobilized at a density between 1,000 RU and 20,000 RU. In some embodiments, the ligand is immobilized at a density between 5,000 RU and 15,000 RU. In some embodiments, the ligand is immobilized at 10,000 RU.

In some embodiments of the system, the biological sample is serum or plasma. In some embodiments of the system, the biological sample is from a human. In some embodiments of the system, the biological sample is diluted prior to being added to the system. In some embodiments the biological sample is diluted 2-fold. In some embodiments, the biological sample is diluted up to 10-fold. In some embodiments, the sample is diluted up to 20-fold. In some embodiments, the sample is diluted up to 100-fold.

In some embodiments, the system comprises a component for providing instructions for adjusting the amount of the antibody in the subject based on the amount detected in the biological sample.

In some embodiments, the system is configured as a surface plasmon resonance chip. In some embodiments, the system further comprises a computer or computers that may be used to implement any of the components of the system. In other embodiments, the system may comprise a computer-program product tangibly embodied in a non-transitory machine-readable storage medium (i.e., software), including instructions configured to cause one or more computers to perform actions to measure the antibody and/or antibody fragment using the system.

In some embodiments of the system, the intra-assay inaccuracy is less than 20%. In some embodiments of the system, the acceptable detected concentration of an antibody is 80-120% of its actual concentration. In some embodiments of the system, the sensitivity for measurement of an antibody or antibody fragment is affected less than 5% by the presence of an interferent. In some embodiments of the system, the LLOQ and ULOQ for certolizumab are 1.0 µg/mL and 90 µg/mL, respectively.

Also disclosed herein are kits for detection of an antibody or an antibody fragment. The kits may comprise a biosensor for SPR having a first binding agent immobilized on one surface; a ligand for the first binding agent, wherein the ligand also binds to the antibody or the antibody fragment. In certain embodiments, the kit may further include a second antibody or a second binding agent that recognizes a moiety on the antibody. Also, in some embodiments, the kit may include reagents for washing the biosensor to remove biomolecules that do not specifically bind to the first binding agent, the ligand, or the antibody and instructions for use.

Thus, in some embodiments, the present disclosure provides for a kit for detection of an antibody or antibody fragment in a biological sample from a subject comprising a biosensor for surface plasmon resonance (SPR) having optionally, a first binding agent immobilized on one surface; a ligand for the first binding agent, wherein the ligand also binds to the antibody or antibody fragment; optionally, a second antibody or a second binding agent that recognizes a moiety on the antibody or antibody fragment; and optionally, reagents for washing the biosensor to remove biomolecules that do not specifically bind to the first binding agent, the ligand, or the antibody. In some embodiments, the antibody is an antibody therapeutic. In some embodiments, the ligand may be directly bound to the bisensor surface (i.e., without the use of a first binding agent). In some embodiments of the kit, the antibody therapeutic is certolizumab. In some embodiments of the kit, the moiety on the antibody is polyethylene glycol (PEG). In some embodiments of the kit, the ligand is TNFα. In some embodiments of the kit, the first binding agent is an antibody. The secondary binding agent or antibody may be used in the embodiment where a first binding agent is used or in the embodiment where the first binding agent is not used (i.e., where the ligand is immobilized directly to the SPR biosensor).

The kit may also include instructions for interpreting the data and positive and/or negative controls. For example, in an embodiment, the positive controls may comprise known concentrations of the antibody or antibody fragment that can be used to prepare a standard curve for comparison to the sample. In an embodiment, the negative control may comprise a sample that is the same matrix (e.g., serum, plasma etc) as the sample, but which is known not to contain the antibody or antibody fragment.

In other embodiments, the kit may comprise a computer-program product tangibly embodied in a non-transitory machine-readable storage medium, including instructions configured to cause one or more computers to perform actions to measure the antibody and/or antibody fragment using the kit.

In some embodiments of the kit, surface plasmon resonance (SPR) provides for real-time detection of the antibody. In some embodiments of the kit, the SPR biosensor comprises metal surface. In some embodiments of the kit, the SPR biosensor comprises a sensor chip. In some embodiments of the kit, the SPR biosensor comprises a thin alginate layer for amine coupling of ligands. In some embodiments of the kit, the sensor chip has a surface coating that can be activated to react specifically with free surface amines of proteins. In some embodiments of the kit, the ligand is immobilized at a density of at least 1,000 Response Units (RU). In some embodiments, the ligand is immobilized at a density between 1,000 RU and 20,000 RU. In some embodiments, the ligand is immobilized at a density between 5,000 RU and 15,000 RU. In some embodiments, the ligand is immobilized at 10,000 RU.

In some embodiments of the kit, the biological sample is serum or plasma. In some embodiments of the kit, the biological sample is from a human. In some embodiments of the kit, the biological sample is diluted and the kit may comprise reagents for dilution. In some embodiments the biological sample is diluted 2-fold. In some embodiments, the biological sample is diluted up to 10-fold. In some embodiments, the sample is diluted up to 20-fold. In some embodiments, the sample is diluted up to 100-fold.

In some embodiments, the kit comprises a component for providing instructions for adjusting the amount of the antibody in the subject based on the amount detected in the biological sample.

In some embodiments, the kit is configured as a surface plasmon resonance chip.

In some embodiments of the kit, the intra-assay inaccuracy is less than 20%. In some embodiments of the kit, the acceptable detected concentration of an antibody is 80-120% of its actual concentration. In some embodiments of the kit, the sensitivity for measurement of an antibody or antibody fragment is affected less than 5% by the presence of an interferent. In some embodiments of the kit, the LLOQ and ULOQ for certolizumab are 1.0 µg/mL and 90 µg/mL, respectively.

In certain embodiments, surface plasmon resonance is used in the system and/or kit for detection of the antibody or antibody fragment. Surface plasmon resonance (SPR) can be used in the disclosed systems and kits to detect changes in optical resonance when an analyte binds to a molecule that has been immobilized on a metal surface. The system and/or kit may be configured so that these reactions are monitored in real time and in a label-free manner as for example, by monitoring a change in refractive index as disclosed herein to produce a sensorgram. The system and/or kit may comprise a computer-program product tangibly embodied in a non-transitory machine-readable storage medium, including instructions configured to monitor the signal and/or to fit the data to an appropriate kinetic binding model. The computer-program product may further calculate kinetic parameters such as the association (ka) and dissociation (kd) rate constants.

In some embodiments, the system and/or kit comprises components to measure a change of the incident angle in response units (RU). 1 RU is $\frac{1}{1,000,000}$ of a refractive index unit, and is roughly equivalent to a surface density of protein at approximately 1 $pg/mm^2$.

The disclosed systems and/or kits may provide for real-time detection of the antibody or antibody fragment. As discussed above, kinetic measurements with SPR may involve sequential injections of analyte over the same ligand surface. Thus, the system and/or kit may comprise components to remove the analyte from the surface so as to regenerate the ligand surface between analyte injections. In some embodiments, the system and/or kit may comprise components to deliver a combination of dilute surfactants, salts, and acids or bases to the surface so as to regenerate the surface as discussed herein. In some embodiments, one or more of the steps can be performed "on-line." The on-line system may comprise an autosampler for removing aliquots of the sample from one container and transferring such aliquots into another container. In such "on-line" systems, the test sample and/or analytes can be passed from one component of the system to another without exiting the system, e.g., without having to be collected and then disposed into another component of the system. In some embodiments, the on-line method is highly automated. In such embodiments, the steps can be performed without the need for operator intervention once the process is set-up and initiated. For example, in one embodiment, the system, or portions of the system may be controlled by a computer or computers. Thus, in certain embodiments, the system may comprise software for controlling the various components of the system, including pumps, valves, autosamplers, and the like. Such software can be used to optimize the extraction process through the precise timing of sample and solute additions and flow rate. Although some or all of the steps in the method and the stations comprising the system may be on-line, in certain embodiments, some or all of the steps may be performed "off-line".

In some embodiments the SPR biosensor of the disclosed system and/or kit comprises a sensor chip. In some embodiments, the SPR biosensor comprises a metal surface. The metal surface can be a thin layer of gold, silver, aluminum, or any other appropriate metal. In some embodiments, the SPR biosensor comprises a thin alginate layer for amine coupling of ligands. As noted above, such sensor chips may be coated with a modified alginate polymer that provides a biomimetic surface for ligand immobilization to reduce or prevent surface denaturation of immobilized ligands, block non-specific analyte binding, and/or allow analyte-ligand binding to occur much as it does in solution. The alginate polymer can be modified with several different functional groups to facilitate different immobilization chemistries. The alginate polymer can be modified with several different functional groups to facilitate different immobilization chemistries. These functional groups can include thiol groups, aldehydes, or any other appropriate functional group. In some embodiments, the sensor chip has a surface coating that can be activated to react specifically with free surface amines of proteins.

In some embodiments, the system and/or kit may comprise components to immobilize the ligand at a density of about 1,000 Response Units (RU). In some embodiments, the ligand is immobilized at a density between 1,000 RU and 20,000 RU. In some embodiments, the ligand is immobilized at a density between 5,000 RU and 15,000 RU. In some embodiments, the ligand is immobilized at 10,000 RU.

In some embodiments, the system and/or kit comprises a first and/or second binding agent that can be, or is, immobilized on a SPR biosensor. The first and/or second binding agent may be provided as a lyophilized powder or in a suitable buffer as is standard in the art. In some embodiments, the first and/or second binding agent is an antibody. In some embodiments, the first binding agent is an anti-TNFα antibody.

In some embodiments, the system and/or kit comprises a reagent comprising a ligand that may be added to bind to a first binding agent immobilized on the SPR biosensor. In some embodiments, the ligand for the first binding agent is TNFα. The ligand may be provided as a lyophilized powder or in a suitable buffer as is standard in the art.

In some embodiments, the system and/or kit may not comprise a first and/or second binding agent and does comprises a reagent comprising a ligand that may be immobilized on the SPR biosensor. In some embodiments, the ligand is TNFα.

Also, the system and/or kit may comprise a reagent comprising a secondary binding agent. Or the secondary binding agent may be provided in solid form (e.g., as a lyophilized powder) or in any other form standard in the art. The second binding agent may recognize a moiety on the antibody, thereby allowing for an enhanced signal to be obtained during SPR. In some embodiments of the present disclosure, the moiety on the antibody is polyethylene glycol (PEG).

The system and/or kit may further comprise reagents for diluting or partially purifying a biological sample. The kit may comprise instructions for performing the disclosed methods or using the disclosed systems.

Computers and Computer Products

In some embodiments, the system and/or kit further comprises a computer and/or a data processor. As disclosed herein, in certain embodiments, the system may comprise one or more computers, and/or a computer product tangibly embodied in a non-transitory computer readable storage medium containing instructions which, when executed on the one or more data processors, cause the one or more data processors to perform actions for performing the methods or implementing the systems and/or kits of any of embodiments disclosed herein. One or more embodiments described herein can be implemented using programmatic modules, engines, or components. A programmatic module, engine, or component can include a program, a sub-routine, a portion of a program, or a software component or a hardware component capable of performing one or more stated tasks or functions. As used herein, a module or component can exist on a hardware component independently of other modules or components. Alternatively, a module or component can be a shared element or process of other modules, programs or machines. For example, as disclosed below, the system and/or kits may comprise a computer and/or computer-program product tangibly embodied in a non-transitory machine-readable storage medium for plotting the SPR signal over time during the interaction between an analyte and a ligand to produce a sensorgram. The system and/or kit may further comprise components to fit the sensorgram data to a binding model to allow for the calculation of the association (ka) and dissociation (kd) rate constants and determination of the binding affinity. Thus, in certain embodiments, the system and/or kit may comprise components to quantify the measurement. Also, the system and/or kit may comprise components to perform statistical analysis of the data so as to determine experimental parameters such as selectivity, sensitivity, accuracy and/or precision.

Thus in certain embodiments, the system and/or kit may comprise components, such as a computer or computer software, to generate a binding model to describe the interaction and affinity of the antibody or antibody fragment for the ligand. Also, in some embodiments, the computer or computer software may be used to perform statistical analysis of the data so as to determine experimental parameters such as selectivity, specificity, sensitivity, accuracy and/or precision. Selectivity can be defined by an antibody's ability to bind a unique epitope. For example, selectivity should be high when an epitope is unique for the protein it is intended to detect. Specificity can be defined by the epitope to which the antibody binds. If the specificity is low, the antibody can bind several different epitopes and vice versa. The sensitivity of an assay can refer to the concentration range within which the assay can accurately detect an antibody. The sensitivity can have a lower limit of quantitation (LLOQ) and an upper limit of quantitation (ULOQ). An assay's accuracy can refer to the closeness of its measured values to a standard or a known value. An assay's precision can refer to the closeness of two or more measurements to each other.

Surface Plasmon Resonance

As discussed in detail herein, the disclosed methods, systems, and kits employ surface plasmon resonance. Surface plasmon resonance (SPR) can detect changes in optical resonance when an analyte binds to a molecule that has been immobilized on a metal surface. In some embodiments, these reactions can be monitored in real time and in a label-free manner. The interactions can be monitored over time by flowing an analyte in a microfluidic channel over a ligand immobilized on a sensor chip and detecting the binding of the analyte to the ligand by measuring changes in the propagation of electromagnetic waves at the sensor surface.

SPR can be used to monitor the complexing of any two unlabeled molecules in real time. In some embodiments, the SPR signal is derived from changes in the refractive index at the surface of a metal sensor chip as an analyte binds to an immobilized ligand. As an analyte flows across the sensor chip, it may bind to a ligand immobilized on the sensor chip, thus changing the refractive index at the surface of the sensor chip. Tracking the change in the SPR signal over time can produce a sensorgram: a plot of the binding response versus time. Furthermore, the sensorgram data can be fitted to an appropriate kinetic binding model to calculate kinetic parameters such as the association (ka) and dissociation (kd) rate constants.

SPR can occur when plane-polarized light at a certain wavelength and angle is reflected off a thin metal film under the condition of total internal reflection. In some embodiments, the SPR system is a prism-based system. As is shown in FIG. 2, light from a light source (210) may shine into a prism (208), causing the light to hit the sensor at a specific angle. Data regarding the intensity of the light reflected off the sensor can then be collected by a detector (209). The light can excite surface plasmons in the metal at a certain incident angle. The excited surface plasmons can be very sensitive to the refractive index change at the surface of the thin metal film. Thus, in some embodiments, the incident angle of the light required for SPR may be impacted by the refractive index change of the molecules in contact with the chip surface. In an SPR binding experiment, this refractive index change can be brought about by binding of analyte in solution to ligand immobilized on the chip surface; therefore, tracking the change in the incident angle required for SPR can allow one to monitor biomolecular interactions in real-time. In some embodiments, the change of the incident angle required for SPR is defined as SPR signal in the unit of response unit (RU). 1 RU is $1/1,000,000$ of a refractive index unit, and is roughly equivalent to a surface density of protein at approximately 1 pg/mm$^2$.

In other embodiments, the SPR system may be an optical fiber-based system, a grating coupled system, an optical waveguide system, or any other SPR system known to one of skill in the art.

In some embodiments, SPR can provide for real-time detection of the antibody or antibody fragment. Generally, the binding response initially increases as analyte is flowed over the sensor chip and associates with the immobilized ligand and then decreases as the analyte solution is replaced with buffer and the binding complex dissociates. Binding equilibrium is reached during the association phase, the sensorgram will reach a constant plateau before the analyte solution is replaced with buffer and the binding complex dissociates. Fitting the sensorgram data to a binding model can allow for the calculation of the association (ka) and dissociation (kd) rate constants and determination of the binding affinity.

Kinetic measurements with SPR may involve sequential injections of analyte over the same ligand surface, which requires complete removal of the analyte, or regeneration of the ligand surface, between analyte injections. In some embodiments, regeneration of the ligand surface is seen in the sensorgram as a sharp drop in RU after dissociation and a return to the original baseline. In some embodiments, regeneration is done with a combination of dilute surfactants, salts, and acids or bases.

In some embodiments, a binding model describing a simple 1:1 interaction may be used where one ligand molecule interacts with one analyte molecule. The complex that forms follows pseudo-first order kinetics, and it can be assumed all binding sites are equivalent and act independently of one another. In some embodiments, complex formation can be described the following equation:

$$A + B \underset{K_d}{\overset{K_a}{\rightleftharpoons}} AB$$

where B represents the ligand and A is the analyte. The rate of formation of the complex is governed by the association rate constant (ka) and the rate of complex dissociation is governed by the dissociation rate constant (kd). Using the above equation, the expected binding response for the association phase, equilibrium (if it is reached during the experiment), and the dissociation phase can be described.

The association phase describes the formation of the binding complex over time as analyte is flowed over the ligand surface. As analyte binds to the ligand immobilized on the sensor chip, there is an associated increase in response units as detected by the change in the SPR signal. The change in the amount of bound complex formed over time is proportional to the association (ka) and dissociation (kd) rate constants with the amount of analyte (A) in excess. Because the binding response in the sensorgram is a measure of the amount of bound complex on the sensor chip, the binding response (in RU) is proportional to the amount of bound complex. During the dissociation phase, analyte may be replaced with a buffer solution and the bound complex dissociates with time. This dissociation can be described by simple first order kinetics. By fitting the relevant equations for the association and dissociation phases to the sensorgram data, one can obtain the kinetic parameters ka and kd for the association and dissociation rate constants, respectively, and the affinity ($K_D$=kd/ka) of the interaction can be calculated. In other embodiments, the affinity of a given interaction is calculated by equilibrium analysis. The equilibrium binding responses at different concentrations can be fit to a simple saturation binding model to extract the affinity ($K_D$).

In some embodiments, the SPR biosensor may comprise a sensor chip. In some embodiments, the SPR biosensor may comprise a metal surface. The metal surface can be a thin layer of gold, silver, aluminum, or any other appropriate metal. In some embodiments, the SPR biosensor may comprise a thin alginate layer for amine coupling of ligands. Sensor chips can come coated with a modified alginate polymer that provides a biomimetic surface for ligand immobilization. The hydrophilic nature of the alginate coating can prevent surface denaturation of immobilized ligands, block non-specific analyte binding, and allow analyte-ligand binding to occur much as it does in solution. The alginate polymer can be modified with several different functional groups to facilitate different immobilization chemistries. These functional groups can include thiol groups, aldehydes, or any other appropriate functional group. In some embodiments, the sensor chip has a surface coating that can be activated to react specifically with free surface amines of proteins.

In some embodiments, the ligand may be immobilized at a density of at least 1,000 Response Units (RU). In some embodiments, the ligand may be immobilized at a density between 1,000 RU and 20,000 RU. In some embodiments, the ligand may be immobilized at a density between 5,000 RU and 15,000 RU. In some embodiments, the ligand may be immobilized at 10,000 RU.

Ligands and Antibodies

In some embodiments, the method may comprise immobilizing a first binding agent on a SPR biosensor. In some embodiments, the first binding agent may be an antibody. In some embodiments, the first binding agent may be an anti-TNFα antibody.

In some embodiments, the method may comprise adding a ligand for the first binding agent under conditions where a complex of the ligand and the first binding agent is formed. In some embodiments, the ligand for the first binding agent may be TNFα. Or, other ligands specific for the antibody or antibody fragment being measured, and appropriate first binding agents that recognize the ligand, may be used.

In some embodiments, the method may comprise not using a first binding agent and immobilizing the ligand on the SPR biosensor. In some embodiments, the ligand may be immobilized to the SPR biosensor is TNFα. Or, other ligands specific for the antibody or antibody fragment being measured may be used.

In some embodiments, the method may comprise adding an aliquot of a biological sample containing an antibody such that the antibody binds to the ligand complexed to the first binding agent. In some embodiments, the method may comprise adding an aliquot of a biological sample containing an antibody such that the antibody binds to the ligand bound to the SPR biosensor. In some embodiments, the antibody or antibody fragment may be an antibody therapeutic. Antibody therapeutics can include, but are not limited to anti-tumor necrosis factor antibodies. Examples include, but are not limited to, monoclonal antibodies such as infliximab, adalimumab, golimumab, and certolizumab pegol. In some embodiments, the antibody therapeutic is certolizumab pegol. Certolizumab pegol is a monoclonal antibody directed against TNFα. More precisely, it is a PEGylated Fab' fragment of a humanized TNF inhibitor monoclonal antibody. The Fab' or human anti-TNF is conjugated with a 40-kDA polyethylene glycol molecule (PEG). The PEGylation of the Fab' fragment changes its physical and chemical properties to improve its pharmacokinetic behavior, typically improving solubility, increasing drug stability, and decreasing immunogenicity. Unlike other TNF inhibitors, certolizumab pegol does not cause complement-dependent cytotoxicity, antibody-dependent cell-mediated cytotoxicity, apoptosis, or necrosis of neutrophils.

In some embodiments, the method may further comprise adding a secondary antibody or a second binding agent that recognizes a moiety on the antibody prior to detecting the final signal obtained from SPR. The secondary binding agent or antibody may be used in the embodiment where a first binding agent is used or in the embodiment where the first binding agent is not used (i.e., where the ligand is immobilized directly to the SPR biosensor). In an embodiment, the secondary binding agent may be an anti-PEG antibody. Or, other secondary binding agents specific for the antibody or antibody fragment being measured may be used.

Biological Samples

In some embodiments, the biological sample may be serum or plasma. In some embodiments, the biological sample may be from a human. In some embodiments, the biological sample may be from a human being treated with an antibody therapeutic. In some embodiments, the biological sample may be neat; in other embodiments, the biological sample may be diluted. In some embodiments the biological sample may be diluted 2-fold. In some embodiments, the biological sample may be diluted up to 10-fold. In some embodiments, the biological sample may be diluted up to 20-fold. In some embodiments, the biological sample may be diluted up to 100-fold.

EXAMPLES

Example 1

Intra- and Inter-Assay Accuracy and Imprecision

The certolizumab pegol by surface plasmon resonance assay is a ligand binding assay used to detect certolizumab pegol in human serum. Certolizumab pegol is a drug that is a PEGylated Fab' fragment of a monoclonal antibody specific to tumor necrosis factor alpha (TNFα).

Anti-TNFα was covalently immobilized onto a SPR biosensor. TNFα was then flowed over the biosensor to act as a capture molecule for the certolizumab pegol in standards, controls, and patient samples. Next, either standards, controls, or unknowns were diluted in phosphate buffer and filtered. Then a diluted standard, control, or unknown was flowed over the biosensor. Finally, an antibody to the certolizumab pegol was flowed over the biosensor to enhance the final signal obtained from the SPR. The final enhanced signal was measured, and the certolizumab pegol concentration in each unknown sample and control is interpolated from a standard curve generated with each assay.

Inaccuracy and imprecision were determined by preparing accuracy and imprecision points independently of the preparation of standard curve calibration lots. Standard matrix is commercially purchased human serum that is pooled. The lower limit of quantitation (LLOQ) for this assay was found to be 1.0 μg/mL, and the upper limit of quantitation (ULOQ) for this assay was found to be 90 μg/mL. Thus, the concentrations of certolizumab pegol tested ranged from 1.0-90 ug/mL. The accuracy and imprecision samples were tested in a total of eight assay batches.

Twenty replicates of the high inaccuracy and imprecision sample (A5-dil at 90 ug/mL) were analyzed in two assay batches.

Each level was analyzed twenty times in one of the assays and at minimum three times in five additional assays. Inaccuracy, expressed as percentage bias, was calculated using Microsoft Excel and the following equation.

$$\text{Inaccuracy (\% bias)} = \frac{\text{Measured Concentration} - \text{Theoretical Concentration}}{\text{Theoretical Concentration}} \times 100$$

Imprecision, expressed as percentage CV, was also calculated using Microsoft Excel and the following equation $$\text{Imprecision (\% } CV) = \frac{\text{Standard Deviation of Data Set}}{\text{Mean of Data Set}} \times 100$$

Total error, expressed as a percentage, was again calculated using Microsoft Excel and the following equation $$\text{Total Error (\%)} = (1.65 \times \% \, CV) + \text{Absolute \% Bias}$$

Acceptance Criteria:

Intra-assay Inaccuracy and Imprecision: Mean bias≤±20% (≤±25% near LLOQ and ULOQ). CV≤20% (≤25% near LLOQ).

At least ⅔ of the replicates must meet bias and CV requirements at each level, with total error≤30% (≤40% near LLOQ and ULOQ).

Inter-assay Inaccuracy and Imprecision: Mean bias≤±20% (≤±25% near LLOQ and ULOQ). CV≤20% (≤25% near LLOQ).

Total error≤30% (≤40% near LLOQ).

Results: The results for Intra- and Inter-assay inaccuracy and imprecision for Certolizumab Pegol are summarized in the table below.

TABLE 1

|  |  | LLOQ 1.0 ug/mL | Low - ULOQ 3.0-90 ug/mL |
|---|---|---|---|
| 20 aliquots in a single batch | Intra-assay Inaccuracy (% bias) | 10.9% | −9.2%-9.1% |
|  | Intra-assay Imprecision (% CV) | 2.1% | 3.1%-4.8% |
|  | Total Error (%) | 14.3% | 5.2%-17.1% |
| 20 aliquots in 1 batch and a minimum of 3 replicates in each of 5 batches | Mean Intra-assay Inaccuracy (% bias) | 15.1% | 0.0%-6.9% |
|  | Mean Intra-assay Imprecision (% CV) | 5.6% | 3.3%-6.5% |
|  | Inter-assay Inaccuracy (% bias) | 13.9% | −3.5%-8.3% |
|  | Inter-assay Imprecision (% CV) | 5.4% | 4.0%-8.0% |
|  | Total Error (%) | 22.9% | 9.5%-20.3% |

Example 2

Selectivity and Specificity

The following potential interferents (i.e., compounds or biomolecules that could interfere with measurement of the antibody) were spiked into human serum containing certolizumab pegol at low and midlevel target levels: Adalimumab, Golimumab, Infliximab, ENBREL®, and Rituximab (and other drugs similar in nature, if available) were analyzed at therapeutic levels. Samples containing interferents were tested in triplicate in a single batch.

Selectivity

To determine whether other similar drugs interfere with the current assay platform samples containing both certolizumab pegol and the interferents were analyzed. The samples were analyzed at low and mid-level certolizumab pegol concentrations, with the interferents analyzed at therapeutic concentrations.

All samples were analyzed in triplicate and mean recovery was based on the certolizumab pegol target concentrations that were calculated based on sample dilutions and or spikes. Acceptable mean recovery from target concentration is 80-120% (75-125% at the LLOQ).

Mean recovery from target was within 80-120% for all interferents analyzed including Adalimumab, Golimumab, Infliximab, Rituximab, and Enbrel. The concentration of certolizumab pegol analyzed ranged from 13.2-48.75 ug/mL.

TABLE 2

| Sample Identification | Potential Interferent Target Concentration (ug/mL) | Certolizumab Pegol Target Concentration (ug/mL) | Calculated Concentration (ug/mL) |
|---|---|---|---|
| Adalimumab-Low Certolizumab Pegol | 10.0 | 17.50 | 7.756* |
|  |  |  | 15.32 |
|  |  |  | 16.68 |
| Mean | NA | 17.50 | 16.00 |
| Mean % Recovery Compared to Target | NA | NA | 91.4% |
| 80% of Target Concentration | NA | 14.00 | NA |
| 120% of Target Concentration | NA | 21.00 | NA |
| Adalimumab-Mid Certolizumab Pegol | 10.0 | 40.00 | 32.74 |
|  |  |  | 34.36 |
|  |  |  | 35.01 |
| Mean | NA | 40.00 | 34.04 |
| Mean % Recovery Compared to Target | NA | NA | 85.1% |
| 80% of Target Concentration | NA | 32.00 | NA |
| 120% of Target Concentration | NA | 48.00 | NA |
| Golimumab-Low Certolizumab Pegol | 2.5 | 15.00 | 15.77 |
|  |  |  | 16.60 |
|  |  |  | 15.44 |
| Mean | NA | 15.00 | 15.94 |
| Mean % Recovery Compared to Target | NA | NA | 106.2% |
| 80% of Target Concentration | NA | 12.00 | NA |
| 120% of Target Concentration | NA | 18.00 | NA |
| Golimumab-Mid Certolizumab Pegol | 2.5 | 48.75 | 43.53 |
|  |  |  | 45.28 |
|  |  |  | 42.06 |
| Mean | NA | 48.75 | 43.62 |
| Mean % Recovery Compared to Target | NA | NA | 89.5% |
| 80% of Target Concentration | NA | 39.00 | NA |
| 120% of Target Concentration | NA | 58.50 | NA |
| Infliximab-Low Certolizumab Pegol | 10.0 | 18.00 | 18.87 |
|  |  |  | 20.01 |
|  |  |  | 20.49 |
| Mean | NA | 18.00 | 19.79 |
| Mean % Recovery Compared to Target | NA | NA | 109.9% |
| 80% of Target Concentration | NA | 14.40 | NA |
| 120% of Target Concentration | NA | 21.60 | NA |
| Infliximab-Mid Certolizumab Pegol | 10.0 | 45.00 | 41.93 |
|  |  |  | 44.58 |
|  |  |  | 42.73 |
| Mean | NA | 45.00 | 43.08 |
| Mean % Recovery Compared to Target | NA | NA | 95.7% |
| 80% of Target Concentration | NA | 36.00 | NA |
| 120% of Target Concentration | NA | 54.00 | NA |
| Rituximab-Low Certolizumab Pegol | 50.0 | 17.50 | 17.85 |
|  |  |  | 19.35 |
|  |  |  | 19.46 |
| Mean | NA | 17.50 | 18.89 |
| Mean % Recovery Compared to Target | NA | NA | 107.9% |
| 80% of Target Concentration | NA | 14.00 | NA |
| 120% of Target Concentration | NA | 21.00 | NA |
| Rituximab-Mid Certolizumab Pegol | 50.0 | 40.00 | 38.46 |
|  |  |  | 39.36 |
|  |  |  | 39.57 |
| Mean | NA | 40.00 | 39.13 |
| Mean % Recovery Compared to Target | NA | NA | 97.8% |
| 80% of Target Concentration | NA | 32.00 | NA |
| 120% of Target Concentration | NA | 48.00 | NA |
| Enbrel-Low Certolizumab Pegol | 2.4 | 13.20 | 12.09 |
|  |  |  | 12.56 |
|  |  |  | 13.16 |
| Mean | NA | 13.20 | 12.60 |
| Mean % Recovery Compared to Target | NA | NA | 95.5% |
| 80% of Target Concentration | NA | 10.56 | NA |
| 120% of Target Concentration | NA | 15.84 | NA |
| Enbrel-Mid Certolizumab Pegol | 2.4 | 42.90 | 36.40 |
|  |  |  | 39.90 |
|  |  |  | 39.28 |
| Mean | NA | 42.90 | 38.53 |
| Mean % Recovery Compared to Target | NA | NA | 89.8% |
| 80% of Target Concentration | NA | 34.32 | NA |
| 120% of Target Concentration | NA | 51.48 | NA |
| Total replicates within 80-120% of target | NA | NA | 100.0% |
| Overall Mean % Recovery Compared to Target | NA | NA | 96.9% |

*Incomplete injection sequence; refer to Sensorgram for Cycle 19

Specificity

Potential interferents (Adalimumab, Golimumab, Infliximab, ENBREL®, and Rituximab) were spiked into human serum free of certolizumab pegol at clinically appropriate levels. The measured concentration was calculated from the standard curve. The percent cross-reaction was calculated as the ratio of the measured concentration to the actual spike concentration of each substance, expressed as a percentage. Insignificant cross-reaction was defined by a value of <5%. Response <LLOQ for potential interferents.

Interference was less than the 1.0 ug/mL, the LLOQ, for all potential interfering substances analyzed.

TABLE 3

| Spiked Substance (Dilutent) | Target Concentration of Spiked Material (ug/mL) | Measured Concentration (ug/mL) | % Recovery of Interferent |
|---|---|---|---|
| Adalimumab (Human Serum) | 20.0 | 0.11850* | 0.6% |
| Golimumab (Human Serum) | 10.0 | 0.03192* | 0.3% |
| Infliximab (Human Serum) | 8.0 | 0.00000* | 0.0% |
| Enbrel (DETEL Sample Diluent) | 8.0 | 0.00000* | 0.0% |
| Rituximab (DRXEC Sample Diluent) | 100.0 | 0.00000* | 0.0% |

*Note that all measured concentrations for the potential interferents were below the limit of quantitation for the assay (1 ug/mL)

Example 3

Examples of Certain Embodiments

Listed hereafter are non-limiting examples of certain embodiments of the technology.

A2. A method for detection of an antibody or antibody fragment in a biological sample from a subject comprising:
immobilizing a first binding agent on a surface plasmon resonance (SPR) biosensor;
adding a ligand that binds to the first binding agent under conditions such that a complex of the ligand and the first binding agent is formed;
adding an aliquot of the biological sample under conditions such that the antibody or antibody fragment binds to the ligand that is complexed to the first binding agent; and
detecting the presence of the antibody or antibody fragment as a change in signal obtained from SPR.

A2. The method of embodiment A1, further comprising adding a secondary antibody or a second binding agent that recognizes a moiety on the antibody or antibody fragment in the biological sample prior to detecting the final signal obtained from SPR.

A3. The method of any of the preceding embodiments, wherein the antibody or antibody fragment is an antibody therapeutic.

A4. The method of embodiment A3, wherein the antibody therapeutic is certolizumab pegol.

A5. The method of A2 to A4, wherein the moiety on the antibody is polyethylene glycol (PEG).

A6. The method of any of the preceding embodiments, wherein the ligand is TNFα.

A7. The method of any of the preceding embodiments, wherein the first binding agent is an antibody.

A8. The method of any of the preceding embodiments, wherein the surface plasmon resonance (SPR) provides for real-time detection of the antibody.

A9. The method of any of the preceding embodiments, wherein the SPR biosensor comprises a sensor chip.

A10. The method of any of the preceding embodiments, wherein the SPR biosensor comprises a metal surface.

A11. The method of any of the preceding embodiments, wherein the SPR biosensor comprises a thin alginate layer for amine coupling of ligands.

A12. The method of embodiment A9, wherein the sensor chip has a surface coating that can be activated to react specifically with free surface amines of proteins.

A13. The method of any of the preceding embodiments, wherein the ligand is immobilized at a density of at least 1,000 Response Units (RU).

A14. The method of any of the preceding embodiments, wherein the biological sample is serum or plasma.

A15. The method of any of the preceding embodiments, wherein the biological sample is from a human.

A16. The method of embodiment A15, wherein the human is being treated with an antibody therapeutic.

A17. The method of any of the preceding embodiments, further comprising adjusting the amount of the antibody in the subject based on the amount detected in the biological sample.

A18. The method of any of the preceding embodiments, wherein the biological sample is diluted at least 2-fold.

A19. The method of any of the preceding embodiments where the intra-assay inaccuracy is less than 20%.

A20. The method of any of the preceding embodiments where the acceptable detected concentration of an antibody is 80-120% of its actual concentration.

A21. The method of any of the preceding embodiments where the sensitivity for measurement of an antibody or antibody fragment is affected less than 5% by the presence of an interferent.

A22. The method of any of embodiments A4 to A21, wherein the LLOQ and ULOQ for certolizumab are 1.0 μg/mL and 90 μg/mL, respectively.

A23. The method of any embodiments A1 to A22, wherein the first binding agent is not used and the ligand is immobilized directly on the SPR biosensor.

A24. The method of any of the preceding embodiments, wherein at least one of the steps is implemented using a computer and/or a computer-program product.

A25. A system for performing the method of any of the preceding embodiments.

B1. A system for detection of an antibody or antibody fragment in a biological sample from a subject comprising:
a biosensor for surface plasmon resonance (SPR) having a first binding agent immobilized on one surface; and
a ligand for the first binding agent, wherein the ligand also binds to the antibody or antibody fragment; and
a component for measuring a signal from the biosensor for surface plasmon resonance.

B2. The system of embodiment B1, wherein the system comprises a second antibody or a second binding agent that recognizes a moiety on the antibody or antibody fragment in the biological sample.

B3. The system of embodiment B1, wherein the system comprises reagents for washing the biosensor to remove biomolecules that do not specifically bind to the first binding agent, the ligand, or the antibody.

B4. The system of embodiment B1, wherein the antibody or antibody fragment is an antibody therapeutic.

B5. The system of embodiment B4, wherein the antibody therapeutic is certolizumab.

B6. The system of embodiments B2 to B5, wherein the moiety on the antibody or antibody fragment is polyethylene glycol (PEG).

B7. The system of embodiments B1 to B6, wherein the ligand is TNFα.

B8. The system of embodiments B1 to B7, wherein the first binding agent is an antibody.

B9. The system of embodiments B1 to B8, wherein the surface plasmon resonance (SPR) provides for real-time detection of the antibody or antibody fragment.

B10. The system of embodiments B1 to B9, wherein the SPR biosensor comprises metal surface.

B11. The system of embodiments B1 to B10, wherein the SPR biosensor comprises a sensor chip.

B12. The system of embodiments B1 to B11, wherein the SPR biosensor comprises a thin alginate layer for amine coupling of ligands.

B13. The system of embodiments B1 to B12, wherein the sensor chip has a surface coating that can be activated to react specifically with free surface amines of proteins.

B14. The system of embodiments B1 to B13, wherein the ligand is immobilized at a density of at least 1,000 Response Units (RU).

B15. The system of embodiments B1 to B14, wherein the biological sample is serum or plasma.

B16. The system of embodiments B1 to B15, wherein the biological sample is from a human.

B17. The system of embodiments B1 to B16, comprising a component for providing instructions for adjusting the amount of the antibody or antibody fragment in the subject based on the amount detected in the biological sample.

B18. The system of embodiments B1 to B17, wherein the biological sample is diluted at least 2-fold.

B19. The system of embodiments B1 to B18, wherein the system is configured as a surface plasmon resonance chip.

B20. The system of embodiments B1 to B19, further comprising a computer and/or computer-program product tangibly embodied in a non-transitory machine-readable storage medium (i.e., software), including instructions configured to cause one or more computers to perform actions to measure the antibody and/or antibody fragment using the system.

B21. The system of any of embodiments B1 to B20, wherein the intra-assay inaccuracy is less than 20%.

B22. The system of any of embodiments B1 to B21, wherein the acceptable detected concentration of the antibody or antibody fragment is 80-120% of its actual concentration.

B23. The system of any of embodiments B1 to B22, wherein the sensitivity for measurement of the antibody or antibody fragment is affected less than 5% by the presence of an interferent.

B24. The system of any of embodiments B5 to B23, wherein the LLOQ and ULOQ for certolizumab are 1.0 µg/mL and 90 µg/mL, respectively.

B25. The system of any embodiments B1 to B24, wherein the first binding agent is not used and the ligand is immobilized directly on the surface of the SPR biosensor.

C1. A kit for detection of an antibody or antibody fragment in a biological sample from a subject comprising:
a biosensor for surface plasmon resonance (SPR) having a first binding agent immobilized on one surface;
a ligand for the first binding agent, wherein the ligand also binds to the antibody or antibody fragment;
optionally, a second antibody or a second binding agent that recognizes a moiety on the antibody or antibody fragment; and
optionally, reagents for washing the biosensor to remove biomolecules that do not specifically bind to the first binding agent, the ligand, or the antibody or antibody fragment; and instructions for use.

C2. The kit of embodiment C1, wherein the antibody or antibody fragment is an antibody therapeutic.

C3. The kit of embodiment C2, wherein the antibody therapeutic is certolizumab.

C4. The kit of embodiments C1 to C3, wherein the moiety on the antibody or antibody fragment is polyethylene glycol (PEG).

C5. The kit of embodiments C1 to C4, wherein the ligand is TNFα.

C6. The kit of embodiments C1 to C5, wherein the first binding agent is an antibody.

C7. The kit of embodiments C1 to C6, wherein the surface plasmon resonance (SPR) provides for real-time detection of the antibody.

C8. The kit of embodiments C1 to C7, wherein the SPR biosensor comprises metal surface.

C9. The kit of embodiments C1 to C8, wherein the SPR biosensor comprises a sensor chip.

C10. The kit of embodiments C1 to C9, wherein the SPR biosensor comprises a thin alginate layer for amine coupling of ligands.

C11. The kit of embodiments C1 to C10, wherein the sensor chip has a surface coating that can be activated to react specifically with free surface amines of proteins.

C12. The kit of embodiments C1 to C11, wherein the ligand is immobilized at a density of at least 1,000 Response Units (RU).

C13. The kit of embodiments C1 to C12, wherein the biological sample is serum or plasma.

C14. The kit of embodiments C1 to C13, wherein the biological sample is from a human.

C15. The kit of embodiments C1 to C14, comprising a component for providing instructions for adjusting the amount of the antibody or antibody fragment in the subject based on the amount detected in the biological sample.

C16. The kit of embodiments C1 to C15, wherein the biological sample is diluted at least 2-fold.

C17. The kit of embodiments C1 to C16, wherein the system is configured as a surface plasmon resonance chip.

C18. The kit of embodiments C1 to C17, further comprising a computer.

C19. The kit of any of embodiments C1 to C18, wherein the intra-assay inaccuracy is less than 20%.

C20. The kit of any of embodiments C1 to C19, wherein the acceptable detected concentration of an antibody or antibody fragment is 80-120% of its actual concentration.

C21. The kit of any of embodiments C1 to C20, wherein the sensitivity for measurement of an antibody or antibody fragment is affected less than 5% by the presence of an interferent.

C22. The kit of any of embodiments C3 to C21, wherein the LLOQ and ULOQ for certolizumab are 1.0 pg/mL and 90 pg/mL, respectively.

C23. The kit of any of embodiments C1 to C22, wherein the first binding agent is not used and the ligand is immobilized directly on the surface of the SPR biosensor.

C24. The kit of any of embodiments C1 to C23, further comprising a computer-program product tangibly embodied in a non-transitory machine-readable storage medium, including instructions configured to cause one or more computers to perform actions to measure the antibody and/or antibody fragment using the kit.

D1. A method for detection of an antibody or antibody fragment in a biological sample from a subject comprising:
immobilizing a ligand on a surface plasmon resonance (SPR) biosensor;
adding an aliquot of the biological sample under conditions such that the antibody or antibody fragment binds to the ligand; and
detecting the presence of the antibody and/or antibody fragment as a change in signal obtained from SPR.

D2. The method of embodiment D1, wherein the antibody is an antibody therapeutic.

D3. The method of embodiment D2, wherein the antibody therapeutic is certolizumab.

D4. The method of embodiments D1 to D3, wherein the ligand is TNFα.

D5. The method of embodiments D1 to D4, further comprising adding a secondary antibody or a second binding agent that recognizes a moiety on the antibody or antibody fragment in the biological sample prior to detecting the final signal obtained from SPR.

D6. The method of embodiment D5, wherein the moiety on the antibody or antibody fragment is polyethylene glycol (PEG).

D7. The method of any of D1 to D6, wherein at least one of the steps is implemented using a computer and/or a computer-program product.

E1. A system for detection of an antibody or antibody fragment in a biological sample from a subject comprising:
a biosensor for surface plasmon resonance (SPR) having a ligand immobilized on one surface wherein the ligand can bind to the antibody or antibody fragment; and
a component for measuring a signal from the biosensor for surface plasmon resonance.

E2. The system of embodiment E1, wherein the antibody is an antibody therapeutic.

E3. The system of embodiment E2, wherein the antibody therapeutic is certolizumab.

E4. The system of embodiments E1 to E3, the ligand is TNFα.

E5. The system of embodiments E1 to E4, further comprising secondary antibody or a second binding agent that recognizes a moiety on the antibody or antibody fragment in the biological sample.

E6. The system of embodiment E5, wherein the moiety on the antibody or antibody fragment is polyethylene glycol (PEG).

E7. The system of embodiments E1 to E6, further comprising a computer and/or computer-program product tangibly embodied in a non-transitory machine-readable storage medium (i.e., software), including instructions configured to cause one or more computers to perform actions to measure the antibody and/or antibody fragment using the system.

F1. A kit for detection of an antibody or antibody fragment in a biological sample from a subject comprising:
a biosensor for surface plasmon resonance (SPR) having a ligand that binds to the antibody or antibody fragment immobilized on one surface;
optionally, a second antibody or a second binding agent that recognizes a moiety on the antibody or antibody fragment; and
optionally, reagents for washing the biosensor to remove biomolecules that do not specifically bind to the first binding agent, the ligand, or the antibody; and instructions for use.

F2. The kit of embodiment F1, wherein the antibody or antibody fragment is an antibody therapeutic.

F3. The kit of embodiment F2, wherein the antibody therapeutic is certolizumab.

F4. The kit of embodiments F1 to F3, the ligand is TNFα.

F5. The kit of embodiments F1 to F4, wherein the moiety on the antibody or antibody fragment is polyethylene glycol (PEG).

F6. The kit of any of F1 to F6, wherein at least one of the steps is implemented using a computer and/or a computer-program product.

That which is claimed is:

1. A method for detection of an antibody or antibody fragment in a biological sample from a subject consisting essentially of:
immobilizing a first binding agent on a surface plasmon resonance (SPR) biosensor;
adding a ligand that binds to the first binding agent under conditions such that a complex of the ligand and the first binding agent is formed;
adding an aliquot of the biological sample under conditions such that the antibody or antibody fragment binds to the ligand that is complexed to the first binding agent, wherein the antibody or antibody fragment is an antibody therapeutic, and wherein the biological sample is from a human being treated with the antibody therapeutic;
adding a secondary antibody or a second binding agent that recognizes a moiety on the antibody or antibody fragment; and
detecting the antibody or antibody fragment as a change in signal obtained from SPR.

2. The method of claim 1, wherein the antibody therapeutic is certolizumab pegol.

3. The method of claim 2, wherein a lower limit of quantitation (LLOQ) and an upper limit of quantitation (ULOQ) for certolizumab are 1.0 μg/mL and 90 μg/mL, respectively.

4. The method of claim 1, wherein the moiety on the antibody or antibody fragment is polyethylene glycol (PEG).

5. The method of claim 1, wherein the ligand is TNFα.

6. The method of claim 1, wherein the first binding agent is an antibody.

7. The method of claim 1, wherein the surface plasmon resonance (SPR) provides for real-time detection of the antibody.

8. The method of claim 1, wherein the SPR biosensor comprises a sensor chip.

9. The method of claim 8, wherein the sensor chip has a surface coating that can be activated to specifically react with free surface amines of proteins.

10. The method of claim 1, wherein the SPR biosensor comprises a metal surface.

11. The method of claim 1, wherein the SPR biosensor comprises an alginate layer for amine coupling of ligands.

12. The method of claim 1, wherein the ligand is immobilized at a density of at least 1,000 Response Units (RU).

13. The method of claim 1, wherein the biological sample is serum or plasma.

14. The method of claim 1, further comprising adjusting the amount of the antibody therapeutic in the subject based on the antibody or antibody fragment detected in the biological sample.

15. The method of claim 1, wherein the biological sample is diluted at least 2-fold.

* * * * *